United States Patent [19]
Jensen et al.

[11] Patent Number: 5,858,332
[45] Date of Patent: Jan. 12, 1999

[54] DENTAL BLEACHING COMPOSITIONS WITH HIGH CONCENTRATIONS OF HYDROGEN PEROXIDE

[75] Inventors: Steven D. Jensen, Midvale; Dan E. Fischer, Sandy, both of Utah

[73] Assignee: Ultradent Products, Inc., South Jordan, Utah

[21] Appl. No.: 781,858

[22] Filed: Jan. 10, 1997

[51] Int. Cl.⁶ .............. A61K 7/16; A61K 7/20; C01B 15/01; C01B 15/055
[52] U.S. Cl. .............. 424/53; 433/216; 252/186.25; 252/186.26; 252/186.29; 252/186.3
[58] Field of Search .......... 252/186.25, 186.26, 252/186.27, 186.28, 186.29, 186.3; 433/215, 216; 424/53, 54, 55, 57, 616

[56] References Cited

U.S. PATENT DOCUMENTS

| | | | |
|---|---|---|---|
| 4,661,070 | 4/1987 | Friedman | 433/203.1 |
| 4,837,008 | 6/1989 | Rudy et al. | 424/53 |
| 5,032,178 | 7/1991 | Cornell | 106/35 |
| 5,059,417 | 10/1991 | Williams et al. | 424/53 |
| 5,094,845 | 3/1992 | Vlock | 424/52 |
| 5,098,303 | 3/1992 | Fischer | 433/215 |
| 5,171,564 | 12/1992 | Nathoo et al. | 424/53 |
| 5,217,710 | 6/1993 | Williams et al. | 424/52 |
| 5,234,342 | 8/1993 | Fischer | 433/215 |
| 5,256,402 | 10/1993 | Prencipe et al. | 424/53 |
| 5,290,566 | 3/1994 | Schow et al. | 424/488 |
| 5,310,563 | 5/1994 | Curtis et al. | 424/616 |
| 5,372,802 | 12/1994 | Barrows et al. | 424/52 |
| 5,376,006 | 12/1994 | Fischer | 433/215 |
| 5,403,578 | 4/1995 | Gordon | 424/53 |
| 5,409,631 | 4/1995 | Fischer | 252/186.25 |
| 5,425,953 | 6/1995 | Sintov et al. | 424/404 |
| 5,578,293 | 11/1996 | Prencipe et al. | 424/49 |
| 5,645,428 | 7/1997 | Yarborough | 433/215 |
| 5,718,886 | 2/1998 | Pellico | 424/53 |
| 5,766,011 | 7/1998 | Signes | 433/215 |

OTHER PUBLICATIONS

Introducing the New, Universal Permulen Polymeric Emulisifiers, BF Goodrich, pp. 1–9, Mar. 1993.
Pemulen Polymeric Emulisifers, Material Safety Data Sheet, BF Goodrich, pp. 1–6, Jul. 1993.

*Primary Examiner*—Joseph D. Anthony
*Attorney, Agent, or Firm*—Workman, Nydegger, Seeley

[57] ABSTRACT

Dental bleaching compositions that include a high concentration of bleaching agent and a bleaching agent stabilizer that maintains the potency of the bleaching agent over time. The dental bleaching compositions of the present invention may be one-part, pre-mixed compositions that do not require mixing at the time of treating a patient's teeth but which remain stable over time. The bleaching agent may consist of hydrogen peroxide, either in aqueous form or complexed with urea (carbamide peroxide) or sodium perborate. The bleaching agent stabilizer includes an impurity scavenger that binds or ties up impurities, such as errant or residual metal ions, that can cause decomposition of the bleaching agent. The bleaching agent stabilizer may include a carboxylic acid chelator or a tin salt. The bleaching composition may include a thickening agent to achieve a selected viscosity and a neutralizing agent to adjust the pH and a carrier to help provide selected consistency and potency. The dental bleaching compositions may be adapted to be loaded into and delivered from a syringe.

34 Claims, No Drawings

DENTAL BLEACHING COMPOSITIONS WITH HIGH CONCENTRATIONS OF HYDROGEN PEROXIDE

BACKGROUND OF THE INVENTION

1. The Field of the Invention

The present invention relates to dental bleaching compositions and methods for treating tooth surfaces. More particularly, the present invention is directed to a stable one-component viscous/gelled dental bleaching composition that has a high concentration of bleaching agent. The dental bleaching compositions of the present invention can optionally include a radiant-energy and/or heat-energy absorbing substance which can absorb these forms of energy and cause the bleaching agent to more quickly bleach the tooth surfaces.

2. The Relevant Technology

The use of certain foods and tobacco, the process of aging, diseases, trauma, medications, some congenital conditions, and environmental effects can cause teeth to become discolored. Because white or whitened teeth are usually considered to be aesthetically superior to stained or discolored teeth, there has been a heightened level of interest of late in developing compositions and methods for bleaching teeth.

A tooth is comprised of an inner dentin layer and an outer hard enamel layer that is slightly porous. The natural color of the tooth is opaque to translucent white or off-white.

Some dentrifices, like toothpastes, gels, and powders, contain active oxygen or hydrogen peroxide liberating bleaching agents. Such bleaching agents include peroxides, percarbonates and perborates of the alkali and alkaline earth metals or complex compounds containing hydrogen peroxide. Also, peroxide salts of the alkali or alkaline earth metals are known to be useful in whitening teeth.

The most commonly used dental bleaching agent is carbamide peroxide ($CO(NH_2)_2.H_2O_2$), also called urea hydrogen peroxide, hydrogen peroxide carbamide, and perhydrolurea. Carbamide peroxide has been used by dental clinicians for several decades as an oral antiseptic. Tooth bleaching was an observed side effect of extended contact time. Over-the-counter compositions of 10% carbamide peroxide are available as "GLY-OXIDE®" by Marion Laboratories and "PROXIGEL®" by Reed and Carnrick. An extended-contact application of bleaching gel held in a dental tray is available as "OPALESCENCE®" by Ultradent. Other bleaching agents such as peroxyacetic acid ($CH_3C=OO-OH$) and sodium perborate, are also known in the medical, dental and cosmetic arts.

Patients who have desired to have their teeth whitened have typically done so by applying a bleaching composition to the teeth by means of the dental tray for repeated treatments, or they had to submit to conventional in-office bleaching techniques that required from 4 to 10 visits to the dental office before clinically significant results were achieved. Less effective teeth whitening was also done by the use of toothpastes or polishes that were applied by brushing. Clinically significant results are quantifiable such as by measuring gray scale, L*, and as to yellowness or blueness, b*, in the CIE® system of color measurement or by equivalent methods.

Bleaching compositions have been manufactured in one-part and two-part systems. A one-part system consists of a compound in which the active bleachant is dispersed into inert components to form an emulsion or gel. One-part systems can also further consist of mixtures in which stabilizers are used to prevent premature decomposition of the peroxide in the bleaching composition. The advantage of a one-part system is ease of use and convenience. The main disadvantage is that prior art one-part viscous/gelled bleaching compositions generally contain relatively low concentrations of peroxide. High concentrations in pre-mixed gels have not been stable. Thus, current one-part systems have a low potency and are slow to react. Most one-part systems in the past have included active peroxide in a range of up to about 3.5% by weight. Due to the relatively low concentration of active bleaching agent in one-part systems, about 10 applications on average are necessary for effective bleaching.

In a two-part system, aqueous hydrogen peroxide is mixed with other components to achieve a preferred higher viscosity. These components are mixed just prior to bleaching due to the incompatibility of the other components with hydrogen peroxide. The main advantage of a two-part system is that it allows for much higher concentrations of active peroxide that cannot exist stably as a one-part system for incidental off-the-shelf use. This results in faster bleaching of the patient's teeth due to the higher peroxide concentration. Faster bleaching is desirable, especially where patient compliance with longer bleaching regimens is problematic, or if only one or a few teeth need individual bleaching.

Another example of a two-part system is microencapsulation of the bleaching agent and a stabilizer. The microcapsules would separate the bleaching agent from the carrier and other materials and would rupture only upon physical shear caused by a tooth brush. The dental bleaching effect of the microencapsulation system is only visible after prolonged use due to its low peroxide concentration or low activation rate.

Although positive results using the foregoing techniques have been reported, the effectiveness of the techniques depends upon such factors as type and intensity of the stain, bleaching agent contact time on the teeth, the amount of available active bleachant in the bleaching agent, and the persistence of the individual in applying the treatment until the desired result is accomplished.

Notwithstanding the foregoing advantages, there remain some important disadvantages to current one-part and two-part systems. A disadvantage to the two-part system is that the bleaching composition must be mixed on-site in the operatory immediately before application to the patient's tooth. Mixing requires additional time by the dental professional, which lowers efficiency and represents an extra preparatory procedure. Mixing in proper amounts is also important in order to yield consistent results.

Another disadvantage where high peroxide concentrations are used is that bleaching compositions that must be mixed on-site in the operatory subject the dental professional to the possibility of burns due to mixing splatter. Additionally, high concentrations of hydrogen peroxide are strong oxidizers.

Another disadvantage with two-part bleaching compositions is that, once mixed, the bleaching compositions must be used soon, since they are unstable and tend to decompose through the release of oxygen from the peroxide moieties. Often, the constituents of the bleaching compositions themselves accelerate decomposition rates. While such accelerants are useful in promoting faster bleaching, they yield a composition having a very short lifespan. Because known accelerants are chemical in nature, they cannot be added until bleaching is to commence. Otherwise the premature release of active oxygen will quickly decrease the potency of the bleaching composition. Moreover some accelerant(s) or peroxide indicators are unstable in that they themselves are consumed by the peroxide. The tendency of prior art accelerants or indicators to be themselves consumed has the effect of reducing the concentration of both the peroxide and the accelerant over a short period of time, thus reducing the effectiveness of each.

From the foregoing, it will be appreciated that what is needed in the art are stable, one-part, pre-mixed viscous/gelled bleaching compositions and methods for treating tooth surfaces that allow for greatly increased bleaching rates compared to existing one-part systems.

Additionally, it would be a significant advancement in the art to provide stable, one-part, pre-mixed viscous/gelled dental bleaching compositions for treating tooth surfaces that included means for accelerating the release of active oxygen from the bleaching agent when needed but which do not cause premature decomposition of the active dental bleaching agent or destruction of the bleaching agent activator.

It would still be a further advancement in the art to provide stable, one-part, pre-mixed viscous/gelled dental bleaching compositions that included higher concentrations of bleaching agent compared to existing one-part compositions that are made at the time of manufacture.

Such stable, one-part, pre-mixed dental bleaching compositions and methods for bleaching tooth surfaces are disclosed and claimed herein.

SUMMARY AND OBJECTS OF THE INVENTION

The present invention comprises stable, one-part, pre-mixed dental bleaching compositions made with a bleaching agent and a radiant-energy absorbing constituent that acts as a bleaching agent activator. The dental bleaching compositions of the present invention are one-part, pre-mixed compositions a with sufficient shelf life to allow for storage in a dental professional's operatory for use when needed. Preferred bleaching agents include peroxides such as hydrogen peroxide and carbamide peroxide (which is a complex between urea and hydrogen peroxide). Preferred bleaching agent activators include radiant-energy absorbing substances, preferably substantially conjugated hydrocarbons such as aromatic rings or conjugated chains, that are stable in the presence of the bleaching agent in varying concentrations and that will not cause premature decomposition of the bleaching agent before the composition has been irradiated with radiant energy.

A thickening agent can be used to give the dental bleaching composition a desired consistency, thickness, and viscosity. Preferred thickening agents include PEMULEN®, a proprietary compound from B.F. Goodrich, or a compositional or chemical equivalent thereof.

An important advantage of the bleaching compositions of the present invention are that they are stable over time. A major cause of premature degradation of the bleaching agent is the existence of errant or residual metal ions that can act as bleaching agent catalysts. Hence, it is possible to create stable bleaching compositions even at high concentrations (greater than 20% by weight) by avoiding, removing, or trapping errant or residual metal ions.

Scavenging of errant or residual metal ions can be accomplished by means of a bleaching agent stabilizer. The bleaching agent stabilizer comprises edetate disodium, EDTA, oxine EDTA, calcium disodium EDTA, adipic acid, succinic acid, citric acid and their respective salts,, tin nitrates, tin phosphates, their combinations, and the like.

Activation of the dental bleaching composition of the present invention is accomplished with a bleaching agent activator that is preferably a radiant-energy or heat-energy absorbing substance. Examples of such substances include radiant-energy absorbing, substantially conjugated hydrocarbons such as aromatic hydrocarbons, multiple double-bond hydrocarbon chains, chain-aromatic mixtures, reacted combinations thereof, and equivalents. Specific examples include caroteneoids such as bixin, lycoxanthin, lycophil, canthaxanthin, capsanthin, cryptoxanthin, isomers of carotene, and lycopene. Other specific examples include aromatics such as coronene, fluoranthene, naphtho[2,3-a]pyrene, trans-4,4'-diphenylstilbene, 9,10-diphenylanthracene, 5,12-bis (phenyethynyl) napthacene, 9,10-bis (phenylethynyl) anthracene, and perylene. The foregoing compounds may optionally include one or more carboxyl groups. The only limitations are (1) that the radiant-energy absorbing substance does not cause substantial peroxide decomposition over time, and (2) that the radiant-energy absorbing substance be substantially peroxide resistant in the presence of the bleaching agent over time. Preferred bleaching agent activators include 9,10-bis (phenylethynyl) anthracene, perylene, and isomers of carotene and carboxyl-substituted variations thereof.

The bleaching compositions preferably include an inert or non-problematic carrier. The carrier may include, but is not limited to water, polypropylene glycol, polyethylene glycol, sorbitol, propylene glycol, glycerol, steryl alcohol, large molecular weight polyols, mixtures of the foregoing, and equivalents.

Because the bleaching compositions of the present invention are both stable in a one-part, pre-mixed system and include the radiant-energy absorbing substance, the bleaching process is greatly simplified. The dental bleaching compositions may advantageously be either pre-loaded or loaded manually into and dispensed from a syringe onto the patient's teeth. The dental professional simply places a desired quantity of the dental bleaching composition on the patient's teeth and then triggers accelerated bleaching by either irradiating the bleaching composition with radiant energy, such as visible and/or UV light, or by applying e.g. conductive heat energy to the composition before, during, or after application to the teeth. Depending on the desired rate of bleaching and patient sensitivity to bleaching agents, a bleaching composition having the optimum amount of bleaching agent can be selected before bleaching commences or can be determined by noting the results of the first bleaching treatment.

In view of the foregoing, it is an object of the present invention to provide stable, one-part, pre-mixed bleaching compositions and methods for treating tooth surfaces that allow for greatly increased bleaching rates compared to existing one-part systems.

It is a further object and feature of the present invention to provide stable, one-part, pre-mixed viscous/gelled dental bleaching compositions for treating tooth surfaces that include means for accelerating the release of active oxygen from the bleaching agent when needed but which does not cause premature decomposition of the active dental bleaching agent or destruction of the bleaching agent activator.

In addition, it is an object of the present invention to provide stable, one-part, pre-mixed viscous/gelled dental bleaching compositions that include higher concentrations of bleaching agent compared to existing one-part compositions. In connection with this object of the present invention, it is an added object of the present invention to provide a high potency, active oxygen liberating bleaching composition that does not require mixing immediately before use, thus avoiding the danger of splatter burns on the clinician or the patient.

These and other objects and features of the present invention will become more fully apparent from the following description and appended claims, or may be learned by the practice of the invention as set forth hereinafter.

DETAILED DESCRIPTION OF THE PREFERRED EMBODIMENTS

The one-part, pre-mixed viscous/gelled dental bleaching compositions of the present invention are comprised of several components that, working in concert, provide a stable and effective viscous/gelled one-part, pre-mixed dental bleaching composition. The inventive bleaching compositions are stable over time but can be caused to accelerate bleaching by means of radiant or heat energy. The components include a bleaching agent, a thickening agent or gelling agent, a neutralizing agent, a carrier, a bleaching agent stabilizer, and a bleaching agent activator. Each component contributes to the dental bleaching composition in different ways.

A. Bleaching Agents.

Preferred bleaching agents include hydrogen peroxide and hydrogen peroxide-containing complexes, such as carbamide peroxide $(NH_2)_2CO—H_2O_2$. Peroxides can provide a ready source of active oxygen in effective concentrations.

Hydrogen peroxide is the preferred bleaching agent in some cases, especially where it is desired to include a relatively high concentration of bleaching agent concentrations. Because of the nature of hydrogen peroxide, it is only available as an aqueous solution. Aqueous available hydrogen peroxide solutions from 3% to 90% by weight hydrogen peroxide are commercially available.

On the other hand, carbamide peroxide can provide a nonaqueous form of available hydrogen peroxide. Carbamide peroxide in its pure form is a crystalline substance consisting of a molecule of urea complexed with a single molecule of hydrogen peroxide. Carbamide peroxide is generally more stable than aqueous hydrogen peroxide and is often preferred for that reason. However, because of the existence of the urea molecule, pure crystalline urea peroxide contains only about 36% available hydrogen peroxide. This means that the upper limit of available peroxide for bleaching when only using carbamide peroxide is lower than 36% when significant quantities of other components such as water, proplyene glycol, or glycerol and the like are included in the bleaching composition.

The type and amount of hydrogen peroxide to be used will depend on the desired peroxide concentration in the final dental bleaching composition. In general, it will be preferable to use concentrated hydrogen peroxide solutions when it is desired to manufacture a bleaching composition having high concentrations of bleaching agent. Lower concentrated hydrogen peroxide solutions and/or carbamide peroxide and/or sodium perborate are generally used when it is desired to manufacture a bleaching composition having lower concentrations of bleaching agent. Carbamide peroxide solutions and hydrogen peroxide solutions can be mixed together in varying concentrations to yield bleaching compositions having a wide spectrum of bleaching agent concentrations. Additionally, sodium perborate can be used alone or it can be mixed with each or both of hydrogen peroxide and carbamide peroxide.

Because hydrogen peroxide is generally less stable with increasing pH, many hydrogen peroxide solutions include acidifying agents such as mineral acids in order to render a more stable hydrogen peroxide solution. However, upon mixing such solutions with the other constituents to yield the dental composition of the present invention, it will generally be desired to adjust the pH to an acceptable pH range in order to protect the patient's teeth and surrounding tissues. The concept of pH adjustment will be discussed herein below.

B. Thickening Agents.

Thickening agents or gelling agents assist to increase viscosity, to facilitate ease of placement, and to assure the composition stays in place during treatment. Thickening agents preferably have the quality of being substantially inert in the presence of, and not readily decomposed by, the bleaching agent. It has been found that thickening agents that are substantially hydrophilic but have a relatively small lipophilic moiety, are preferred in the present invention. For example, a preferred thickening agent is an emulsifier comprising a high molecular weight polyacrylic acid polymer or copolymer.

As an example of a preferred thickening agent, we have found that PEMULEN® or a compositional or chemical equivalent thereof possesses the qualities required for the inventive composition. A more preferred thickening agent is PEMULEN® TR-1NF. PEMULEN® is a propriety formula that includes a significant quantity of a polyacrylic copolymer that has a slightly hydrophobic end and a strongly hydrophilic end.

In addition to PEMULEN® or a compositional or chemical equivalent thereof, we have found that silicates may be used; however, the composition loses its gell like qualities that are preferred during application.

C. Neutralizing Agents.

In light of the acidity of some hydrogen peroxide solutions and polyacrylic acid thickeners such as PEMULEN or a compositional or chemical equivalent thereof, it is usually desired to use a neutralizing agent to adjust the pH to within an acceptable pH range. Raising the pH causes some thickeners to become more viscous. In addition, bleaching compositions that are too acidic can etch the patient's teeth and cause irritation to surrounding dental tissues. In most cases, the pH will be in a range from about 2 to about 9, more preferably in a range from about 3 to about 7, and most preferably from about 4 to about 6. Preferred neutralizing agents include alkali hydroxides, such as sodium hydroxide and potassium hydroxide, amines such as diisopropanol amine and triethanol amine, ammonium hydroxide, and the like. The most preferred neutralizing agent is sodium hydroxide, 50 percent in distilled or deionized water.

D. Carriers.

The carrier is used to complement the other dental bleaching composition components and effect good dispersion and stability of the resulting compositions. By adjusting the amount of carrier, the bleaching agent concentration can be adjusted to a selected level. The use of a carrier or carrier combinations aligned with a thickening agent allows for achievement of a selected bleaching agent concentration and a selected consistency. Water, or water in combination with other components including other carriers is sometimes used. Other carriers include polyols, such as polypropylene glycol and polyethylene glycol, sorbitol, propylene glycol, glycerol, steryl alcohol, ethylene glycol, large molecular weight polyols and the like and mixtures of the above. Although ethylene glycol could work as a carrier, it is not used because it is toxic.

E. Bleaching Agent Stabilizers.

The bleaching agent stabilizers act as impurity scavengers that bind with errant or residual metal ions and other impurity elements that might cause decomposition of the bleaching agent. The stabilizer also must not itself be a source of bleaching agent instability. Where an excess of stabilizer is in solution such that all impurities have been bound up by the stabilizer, the excess stabilizer must itself be inert to the bleaching agent. At least two classes of bleaching agent stabilizers are part of the present invention. One class comprises carboxylic acid chelators, such as edetate disodium, EDTA, oxine EDTA, calcium disodium EDTA, adipic acid, succinic acid, citric acid, and the like and mixtures thereof, their respective salts or derivatives. Another class of bleaching agent stabilizers consists of tin-containing salts, such as tin nitrates, tin phosphates, and the like.

F. Bleaching Agent Activators.

Several bleaching agent activators are disclosed in the present invention such as radiant or thermal energy absorbable bleaching agent activators. The preferred qualities of bleaching agent activators include inertness to the bleaching agent and the ability to absorb energy and heat up, thus activating the bleaching agent.

Inert particles that act as a heat sink may also be used. These particles may absorb radiant or conducted thermal energy in such a way so as to not substantially chemically react with the peroxide during application. Such particles may include metals coated with inert films or metal-filled plastic resins.

It has been found that radiant energy absorbable, substantially conjugated hydrocarbons are the preferred bleaching agent activators since they appear to be significantly stable in the presence of peroxides. In other words, they themselves resist oxidation or bleaching in the presence of the bleaching agent.

Preferred bleaching agent activators are defined as substantially conjugated hydrocarbons such as multiple benzene structures, conjugated hydrocarbon chains, and combinations thereof that absorb portions of the electromagnetic spectrum and that have simple hydrogen, hydroxyl, or carboxylic groups attached to the structures and that act as energy-absorbing substances.

The preferred multiple benzene structures can be as simple as naptha-based structures or anthracene-based structures. Useful substantially conjugated hydrocarbons that are benzene structures include 9,10-bis(phenylethynyl)-anthracene, perylene, naphtho[2,3-a]pyrene, trans-4,4'-diphenylstilbene, 9,10-diphenylanthracene, 5,12-bis(phenyethynyl)-napthacene, coronene, fluoranthene, and equivalents.

The known substantially conjugated bond hydrocarbon chains include caroteneoids, such as bixin, lycoxanthin, lycophil, canthaxanthin, capsanthin, cryptoxanthin, isomers of carotene, and lycopene. Of the known substantially conjugated hydrocarbons, 9,10-bis (phenylethynyl)-anthracene, perylene, and isomers of carotene are preferred. Of the known substantially conjugated hydrocarbons, carboxyl-substituted hydrocarbons are also preferred.

Less preferred aromatic compositions such as 7-diethylamino 4-methyl coumarin, henna, and alizarin are less stable compared to the above-defined substantially conjugated hydrocarbons. Henna, a red dye known for at least 4,000 years, is a double-ketonated naphtha hydroxide. Alizarin, a red dye, is a double-ketonated anthracene meta double hydroxide. Although 7-diethylamino 4-methyl coumarin, henna, and alizarin are less preferred, to the extent that one were to use these substances within a stable, one-part, pre-mixed bleaching composition, such a composition would certainly be within the scope of the present invention.

Other substantially conjugated hydrocarbon structures that resist oxidation by peroxides are within the skill of the routineer in the art to find during routine experimentation after consultation with the present invention disclosure or by practicing the invention.

The bleaching agent activators in the dental bleaching composition of the present invention will preferably not only efficiently absorb radiant energy but also preferably will not significantly contribute to bleaching agent decomposition while the composition sits on the shelf. In this way, the inventive bleaching composition will have substantially the same shelf life as a bleaching composition that does not include the bleaching agent activator when stored at an appropriate temperature, e.g. 4° C. In addition to on-the-shelf inertness, it is also preferable that upon application of radiant energy, the bleaching agent activator itself does not substantially react with the oxidizer. The effect of a bleaching agent activator that resists oxidation during patient treatment is an increase in available activator relative to the remaining unreacted bleaching agent.

As radiant energy is applied to the dental bleaching composition, the bleaching agent activator begins to heat up and to accelerate the release of active oxygen from the bleaching agent.

G. General Properties.

To make the dental bleaching composition of the present invention a viable off-the-shelf product for dental professionals, hydrogen peroxide decomposition must be minimized during storage. Because hydrogen peroxide decomposition is accelerated by increasing the temperatures, it is appropriate to store the inventive dental bleaching composition within an appropriate temperature range. e.g. about 4° C. A preferred shelf life is at least about one month, where the amount of available bleaching agent is at least about 95% of the original concentration. For about two months, it is preferable for there to remain at least about 90% of the original available bleaching agent. For about three months, it is preferable for there to remain at least about 80% of the original available bleaching agent.

Obviously, it will generally always be preferable to have more stable systems in which most, if not all, of the bleaching agent remains active over the length of the shelf life. It has been observed that dental bleaching compositions of the present invention remained substantially undecomposed for about three months. For example, samples of the inventive dental bleaching composition were stored refrigerated for 92 days and there remained about 99% of the original available hydrogen peroxide. Samples of the inventive dental bleaching composition were stored refrigerated for 127 days and there remained above 98% of the original available hydrogen peroxide. Additionally, samples of the inventive dental bleaching composition were stored unrefrigerated for 92 days and there remained about 95% of the original available hydrogen peroxide. Because periodic testing of available hydrogen peroxide revealed slow decomposition of the bleaching agent after about three months, it is within the contemplation of the present invention that if refrigerated, uncontaminated, and light-shielded, the inventive dental bleaching composition will contain about 50%, preferably about 90%, and most preferably about 95% of the original available hydrogen peroxide for about one year.

Stability of a dental bleaching composition with about 35% available hydrogen peroxide, wherein the dental bleaching agent maintains at least about 85% of its original strength about one month after manufacture, is understood to be a composition that would contain about 30% available hydrogen peroxide.

The dental bleaching compositions of the present invention can be made such that they include from about 20% to about 90% available hydrogen peroxide; from about 0.05% to about 5% thickening agent; from about 0% to about 10% neutralizing agent; from about 5% to about 80% carrier; from about 0.01% to about 5% stabilizer; and from about 0.001% to about 3% bleaching agent activator.

More preferred dental bleaching compositions of the present invention can be made such that they include from about 25% to about 80% available hydrogen peroxide; from about 0.5% to about 4% thickening agent; from about 0.5% to about 5% neutralizing agent; from about 10% to about 75% carrier; from about 0.1% to about 3% stabilizer; and from about 0.02% to about 2% bleaching agent activator.

Most preferred dental bleaching compositions of the present invention can be made such that they include from about 30% to about 60% available hydrogen peroxide; from about 1% to about 3% thickening agent; from about 0.6% to about 3% neutralizing agent; from about 15% to about 65% carrier; from about 0.5% to about 2% stabilizer; and from about 0.05% to about 1% bleaching agent activator.

H. Methods of Use.

In light of the foregoing inventive features of the dental compositions of the present invention, the method for bleaching teeth is performed in the dental operatory under ordinary conditions. The dental professional applies a layer of the inventive dental bleaching composition on the labial surfaces of as many of the teeth as are desired to be bleached.

Thereafter, rapid bleaching is carried out by irradiating the teeth with radiant energy, such as visible and/or UV radiant energy, to accelerate decomposition of the bleaching agent. The radiant energy excites the dental bleaching activator, which causes the molecular bonds within the activator to vibrate vigorously and heat up the composition. The heated composition causes the accelerated release of free radical oxygen from the dental bleaching agent. The rate of heating can be controlled by the amount of light that is used.

The dental bleaching compositions may advantageously be loaded into and dispensed from a syringe onto the patient's teeth.

I. Examples of the Preferred Embodiments.

In order to more fully teach the present invention, the following examples are presented. The examples are intended to be illustrative only and are certainly not intended to imply that other embodiments not specified are not within the scope of the present invention. Bleaching compositions were prepared according to the present invention and included the components and amounts set forth as Examples 1–28, which are set forth below in Table 1.

In order to illustrate one exemplary manner of mixing together the components, attention is turned to Example 4, in which 254 g of propylene glycol was placed in a container and mixed with 12 g of PEMULEN® TR-1NF until homogenous. Next, stabilizers comprising 8 g each of edetate disodium and citric acid were mixed with water and added as stabilizers to the glycol-PEMULEN mixture to scavenge errant or residual metal ions. Thereafter, 4 g of beta carotene was added as the bleaching agent activator. Following addition of the bleaching agent activator, 705 g of 50% aqueous hydrogen peroxide was added. To the mixture was added 9 g of sodium hydroxide, 50% in water, and the resulting mixture was stirred until homogeneous. The other examples were mixed together in similar fashion, although the concentrations and identities of the components were altered in order to form the compositions as achieved.

Table 1 represents 28 exemplary compositions that were prepared according to the present invention and identified as Examples 1–28. In each sample, the bleaching agent was added in the form of aqueous hydrogen peroxide; therefore the number under the heading "$H_2O_2$" represents the net amount of hydrogen peroxide in the composition. Thus, the balance of the aqueous hydrogen peroxide was water. The thickener was PEMULEN® TR-1NF unless otherwise noted. The neutralizing agent was sodium hydroxide in 50% water. Other components are noted at the foot of Table 1.

TABLE 1

| Example | Active $H_2O_2$ | Water | Thickener | NaOH | Carrier | Stabilizer | Activator | Total |
|---|---|---|---|---|---|---|---|---|
| 1 | 30.25 | 30.25 | 1.2 | 0.9 | 36.4[1] | 1.0[2] | — | 100.0 |
| 2 | 30.5 | 30.5 | 1.5 | 0.8 | 36.7[3] | — | — | 100.0 |
| 3 | 30.5 | 30.5 | 1.2 | 0.9 | 36.9[4] | — | — | 100.0 |
| 4 | 35.25 | 35.25 | 1.2 | 0.9 | 25.4[1] | 1.6[5] | 0.4[6] | 100.0 |
| 5 | 35.25 | 35.25 | 1.2 | 0.9 | 27.4[3] | — | — | 100.0 |
| 6 | 35.25 | 35.25 | 1.2 | 0.9 | 27.4[4] | — | — | 100.0 |
| 7 | 35.25 | 35.25 | 1.2 | 0.9 | 27.4[6] | — | — | 100.0 |
| 8 | 35.25 | 35.25 | 1.2 | 0.9 | 27.3[3] | 1.0[2] | — | 100.0 |
| 9 | 35.25 | 35.25 | 1.2 | 0.9 | 27.2[3] | 0.2[2] | — | 100.0 |
| 10 | 35.25 | 35.25 | 1.2 | 0.9 | 26.4[1] | 1.0[2] | — | 100.0 |
| 11 | 35.25 | 35.25 | 1.2 | 0.9 | 26.4[4] | 1.0[2] | — | 100.0 |
| 12 | 35.25 | 35.25 | 1.2 | 0.9 | 26.0[1] | 1.0 | 0.4[7] | 100.0 |
| 13 | 35.25 | 35.25 | 1.2 | 0.9 | 26.0[1] | 1.4[8] | — | 100.0 |
| 14 | 35.25 | 35.25 | 1.2 | 0.9 | 25.9[1] | 1.5[9] | — | 100.0 |
| 15 | 35.25 | 35.25 | 1.2 | 0.9 | 25.5[1] | 1.5[9] | 0.4[10] | 100.0 |
| 16 | 35.25 | 35.25 | 1.2 | 0.9 | 25.8[1] | 1.5[9] | 0.1[10] | 100.0 |
| 17 | 35.25 | 35.25 | 1.2 | 0.9 | 25.5[1] | 1.8[11] | 0.1[10] | 100.0 |
| 18 | 35.25 | 35.25 | 1.2 | 0.9 | 25.7[1] | 1.6[12] | 0.1[10] | 100.0 |
| 19 | 35.25 | 35.25 | 1.2 | 0.9 | 25.7[1] | 1.8[13] | 0.1[10] | 100.0 |
| 20 | 35.25 | 35.25 | 1.2 | 0.9 | 25.0[1] | 2.3[14] | 0.1[10] | 100.0 |
| 21 | 35.25 | 35.25 | 1.2 | 0.5 | 26.1[1] | 1.8[13] | 0.1[10] | 100.0 |
| 22 | 35.25 | 35.25 | 1.2 | 0.9 | 25.3[1] | 2.0[15] | 0.1[10] | 100.0 |
| 23 | 35.25 | 35.25 | 1.2 | 0.5 | 25.7[1] | 2.0[15] | 0.1[10] | 100.0 |
| 24 | 35.25 | 35.25 | 1.2 | 0.9 | 25.5[1] | 1.8[16] | 0.1[10] | 100.0 |
| 25 | 35.25 | 35.25 | 1.2 | 1.3 | 25.1[1] | 1.8[13] | 0.1[10] | 100.0 |
| 26 | 35.25 | 35.25 | 1.2 | 0.9 | 25.1[1] | 2.2[17] | 0.1[10] | 100.0 |
| 27 | 40.25 | 40.25 | 1.2 | 0.9 | 17.4[3] | — | — | 100.0 |
| 28 | 40.25 | 40.25 | 1.2 | 0.9 | 17.4[4] | — | — | 100.0 |

[1]Propylene glycol; [2]Adipic acid:succinic acid 1:1; [3]Distilled water; [4]Glycerine; [5]Edetate disodium:citric acid 1:1; [6]Polyethylene glycol 300; [7]Bis (phenylethynyl)-anthracene; [8]Edetate disodium:adipic acid:succinic acid 0.8:1:1; [9]Edetate disodium:adipic acid:succinic acid 1:1:1; [10]Perylene; [11]Edetate disodium:adipic acid:succinic acid 1:6:1:1; [12]Edetate disodium:citric acid 1:1; [13]Edetate disodium; [14]Edetate disodium:adipic acid:succinic acid:citric acid 1:6:1:1:1:1; [15]Edetate disodium:EDTA 1:1; [16]Citric acid:EDTA 0.8:1; [17]Edetate disodium:citric acid 1.75:1.

Of the foregoing, Example Nos. 2, 3, 5–7, 27 and 28 were prepared without using any stabilizer and without any bleaching agent activator. Upon measuring the concentration of active hydrogen peroxide over time, it was found that the hydrogen peroxide in these examples was not as stable as those formed with a stabilizer. The rate of decomposition was observed to increase as the concentration of hydrogen peroxide increased. This increased decomposition rate demonstrates the importance of the bleaching agent stabilizer in the event that a stable, one-part, pre-mixed bleaching composition is desired, particularly at higher concentrations of peroxide. These stabilizer-less compositions were also slow to react when irradiated with radiant energy and/or UV light from a standard dental curing light since they included no bleaching agent activator. Hence, in those cases where accelerated bleaching is desired, as opposed to slower but more steady bleaching, it is important to include the bleaching agent activator.

Of the foregoing examples set forth in Table 1, Example Nos. 1, 8–11, and 13–14 were made without any bleaching agent activator but did include a stabilizer, or a combination of stabilizers, according to the present invention. Upon measuring the concentration of active hydrogen peroxide over time it was found that the concentration of hydrogen peroxide in these examples remained above 90% of the original concentration after 28 days of storage. As in Example Nos. 2, 3, 5–9, 27 and 28, these compositions were slow to become activated when irradiated with visible and/or UV light using a commercial dental curing light. However, upon irradiating the compositions with heat energy using a heat lamp that emitted in the infrared range, accelerated decomposition of bleaching compositions within about 1 minute was observed.

Of the foregoing examples set forth in Table 1, Example Nos. 4, 12 and 15–26 were made to contain both a stabilizer and a bleaching agent activator according to the present invention. Upon measuring the concentration of active hydrogen peroxide over time it was found that the concentration of hydrogen peroxide in these examples remained above about 90% of the original concentration after 28 days of storage. Upon measuring the concentration of activator over time it was found that the concentration of the bleaching agent activator color remained virtually unchanged after 28 days of storage at an appropriate temperature, e.g. 4° C. Upon irradiating these compositions with visible and/or UV light using a commercial dental curing light, the compositions became activated. Because the concentration of activator remained stable over time, the slight drop in apparent stability of the hydrogen peroxide compared to compositions in which no activator was used was apparently due to the fact that the compositions were not prepared or stored in total darkness.

Although the use of a heat lamp caused the bleaching compositions to become activated, it is not particularly feasible to place a heat lamp near or inside a patient's mouth. Doing so might cause discomfort or injury. On the other hand, the use of visible and/or UV emitting lamps caused little if any discomfort since the heat that was generated was limited to within the bleaching composition as a result of the radiant-energy absorbing substance activator, and even that heat was mild compared to the heat generated by a heat lamp.

In order to more fully teach the invention, the following hypothetical examples are presented. While the compositions of the following examples were not actually physically mixed together, they were derived or extrapolated from actual mix designs and are based on the results determined by observing the behaviors of actual mix designs.

Examples 29–41 are made according to the mixing sequence set forth above for Example 4, except that the identities and concentrations of the various components are altered as set forth in Table 2 below.

TABLE 2

| Example | Active $H_2O_2$ | Water | Thickener | NaOH | Carrier | Stabilizer | Activator | Total |
|---|---|---|---|---|---|---|---|---|
| 29 | 3.5 | 3.5 | 1.2 | 0.8 | 90.0[1] | 1.0[2] | — | 100.0 |
| 30 | 10 | 10 | 1.2 | 0.8 | 76.9[1] | 1.0[2] | 0.1[10] | 100.0 |
| 31 | 20 | 20 | 1.2 | 0.8 | 57.0[1] | 1.0[2] | — | 100.0 |
| 32 | 20 | 20 | 1.2 | 0.8 | 56.9 | 1.0[2] | 0.1[10] | 100.0 |
| 33 | 25 | 25 | 1.2 | 0.8 | 47.0 | 1.0[2] | — | 100.0 |
| 34 | 25 | 25 | 1.2 | 0.8 | 46.9 | 1.0[2] | 0.1[10] | 100.0 |
| 35 | 40.25 | 40.25 | 1.2 | 0.9 | 16.0[1] | 1.3[2] | 0.1[10] | 100.0 |
| 36 | 50.0 | 33.4 | 1.2 | 0.9 | 11.6[1] | 2.8[2] | 0.1[10] | 100.0 |
| 37 | 55.0 | 29.9 | 1.2 | 1.2 | 9.5[1] | 3.1 | 0.1[10] | 100.0 |
| 38 | 60.0 | 26.4 | 1.2 | 1.3 | 7.6[1] | 3.4 | 0.1[10] | 100.0 |
| 39 | 70.0 | 19.4 | 1.2 | 1.6 | 19.6[1] | 3.9 | 0.1[10] | 100.0 |
| 40 | 80.0 | 12.4 | 1.2 | 1.8 | — | 4.5 | 0.1[10] | 100.0 |
| 41 | 90.0 | 1.9 | 1.2 | 1.8 | — | 5.0 | 0.1[10] | 100.0 |

[1]Propylene glycol; [2]Adipic acid:succinic acid 1:1; [10]Perylene.

Of the foregoing, Example Nos. 29, 31 and 33 are made without any bleaching agent activator but do include a stabilizer or a combination of stabilizers according to the present invention.

Of the foregoing compositions, Example Nos. 30, 32, and 34–41 include both a stabilizer and a bleaching agent activator according to the present invention. The hydrogen peroxide concentration in these examples remains at a level of at least about 80% of the original concentration after 28 days of storage, while the bleaching agent activator color remains virtually unchanged after 28 days of storage. When irradiated, each of the compositions in these examples is activated.

The present invention may be embodied in other specific forms without departing from its spirit or essential characteristics. The described embodiments are to be considered in all respects only as illustrated and not restrictive. The scope of the invention is, therefore, indicated by the appended claims and their combination in whole or in part rather than by the foregoing description. All changes that come within the meaning and range of equivalency of the claims are to be embraced within their scope.

What is claimed and desired to be secured by United States Letters Patent is:

1. A stable, one-part dental bleaching composition for bleaching a person's teeth comprising a bleaching agent, a bleaching agent stabilizer, and a thickening agent, wherein the dental bleaching agent maintains at least 60% of its original strength about three months after manufacture of the bleaching composition and wherein the bleaching agent provides available hydrogen peroxide when initially applied to the person's teeth in a concentration of at least about 20% by weight of the bleaching composition.

2. A stable, one-part dental bleaching composition as defined in claim 1, wherein the hydrogen peroxide maintains at least about 95% of its original strength about one month after manufacture of the bleaching composition.

3. A stable, one-part dental bleaching composition as defined in claim 1, wherein the dental bleaching agent comprises aqueous hydrogen peroxide.

4. A stable, one-part dental bleaching composition as defined in claim 1, wherein the dental bleaching agent comprises carbamide peroxide.

5. A stable, one-part dental bleaching composition as defined in claim 1, wherein the dental bleaching agent comprises sodium perborate.

6. A stable, one-part dental bleaching composition as defined in claim 1, wherein the bleaching agent provides available hydrogen peroxide in a range from about 20% to about 90% by weight of the dental bleaching composition when initially applied to the person's teeth.

7. A stable, one-part dental bleaching composition as defined in claim 1, wherein the bleaching agent provides available hydrogen peroxide in a range from about 25% to about 80% by weight of the dental bleaching composition when initially applied to the person's teeth.

8. A stable, one-part dental bleaching composition as defined in claim 1, wherein the bleaching agent provides available hydrogen peroxide in a range from about 30% to about 60% by weight of the dental bleaching composition when initially applied to the person's teeth.

9. A stable, one-part dental bleaching composition as defined in claim 1, wherein the bleaching agent stabilizer comprises a metal ion scavenger.

10. A stable, one-part dental bleaching composition as defined in claim 1, wherein the dental bleaching agent maintains at least about 80% of its original strength about three months after manufacture of the bleaching composition.

11. A stable, one-part dental bleaching composition as defined in claim 1, wherein the dental bleaching agent maintains at least about 90% of its original strength about three months after manufacture of the bleaching composition.

12. A stable, one-part dental bleaching composition as defined in claim 1, wherein the composition maintains a flowable, gel-like consistency.

13. A stable, one-part dental bleaching composition as defined in claim 1, wherein the thickening agent comprises a polyacrylic acid polymer or copolymer that has a lipophilic portion and a hydrophilic portion.

14. A stable, one-part dental bleaching composition as defined in claim 1, further including a radiant energy absorbing constituent that acts as a bleaching agent activator.

15. A stable, one-part dental bleaching composition as defined in claim 1, wherein the bleaching agent stabilizer comprises a tin salt.

16. A stable, one-part dental bleaching composition as defined in claim 15, wherein the tin salt is selected from the group consisting of tin nitrates, tin phosphates, and mixtures of the foregoing.

17. A stable, one-part dental bleaching composition as defined in claim 1, further including a carrier.

18. A stable, one-part dental bleaching composition as defined in claim 17, wherein the carrier is selected from the group consisting of water, polypropylene glycol, polyethylene glycol, sorbitol, propylene glycol, glycerol, sterol alcohol, large molecular weight polyols, and mixtures of the foregoing.

19. A stable, one-part dental bleaching composition as defined in claim 1, further including a neutralizing agent.

20. A stable, one-part dental bleaching composition as defined in claim 19, wherein the neutralizing agent is included such that the dental bleaching composition has a pH in a range from about 2 to about 9.

21. A stable, one-part dental bleaching composition as defined in claim 19, wherein the neutralizing agent is included such that the dental bleaching composition has a pH in a range from about 3 to about 7.

22. A stable, one-part dental bleaching composition as defined in claim 19, wherein the neutralizing agent is included such that the dental bleaching composition has a pH in a range from about 4 to about 6.

23. A stable, one-part dental bleaching composition as defined in claim 1, wherein the bleaching agent stabilizer comprises a carboxylic acid chelator.

24. A stable, one-part dental bleaching composition as defined in claim 23, wherein the carboxylic acid chelator is selected from the group consisting of edetate disodium, EDTA, oxine EDTA, calcium disodium EDTA, adipic acid, succinic acid, citric acid, salts of the foregoing, and mixtures of the foregoing.

25. A stable, one-part dental bleaching composition for bleaching a person's teeth comprising a bleaching agent, a thickening agent, a carrier, and a bleaching agent stabilizer selected from the group consisting of carboxylic acid chelators and tin salts, wherein the dental bleaching agent maintains at least 60% of its original strength about three months after manufacture of the bleaching composition and wherein the bleaching agent provides available hydrogen peroxide when initially applied to the person's teeth in a concentration of at least about 20% by weight of the bleaching composition.

26. A stable, one-part dental bleaching composition as defined in claim 25, wherein the hydrogen peroxide maintains at least about 95% of its original strength about one month after manufacture of the bleaching composition.

27. A stable, one-part dental bleaching composition as defined in claim 25, wherein the bleaching agent is sold premixed with the thickening agent, the carrier, and the bleaching agent stabilizer.

28. A stable, one-part dental bleaching composition as defined in claim 25, wherein the dental bleaching agent is selected from the group consisting of aqueous hydrogen peroxide, carbamide peroxide, sodium perborate, and mixtures thereof.

29. A stable, one-part dental bleaching composition as defined in claim 25, further including a radiant energy absorbing constituent that acts as a bleaching agent activator.

30. A stable, one-part dental bleaching composition for bleaching a person's teeth comprising a bleaching agent, a thickening agent, and a bleaching agent stabilizer, wherein the dental bleaching agent maintains at least 60% of its original strength about three months after manufacture of the bleaching composition and wherein the bleaching agent provides available hydrogen peroxide when initially applied to the person's teeth in a concentration of at least about 30% by weight of the bleaching composition.

31. A stable, one-part dental bleaching composition for bleaching a patient's teeth as defined in claim 30, wherein the hydrogen peroxide maintains at least about 95% of its original strength about one month after manufacture of the bleaching composition.

32. A stable, one-part dental bleaching composition as defined in claim 30, wherein the bleaching agent is sold premixed with the thickening agent, a carrier, and the bleaching agent stabilizer.

33. A one-part dental bleaching composition as defined in claim 30, wherein the dental bleaching agent is selected from the group consisting of aqueous hydrogen peroxide, carbamide peroxide, sodium perborate, and mixtures thereof.

34. A dental bleaching composition as defined in claim 30, wherein the stabilizing agent is selected from the group consisting of edetate disodium, EDTA, oxine EDTA, calcium disodium EDTA, adipic acid, succinic acid, citric acid, salts of the foregoing, tin nitrates, tin phosphates, and mixtures of the foregoing.

* * * * *

UNITED STATES PATENT AND TRADEMARK OFFICE
CERTIFICATE OF CORRECTION

PATENT NO. : 5,858,332
DATED : January 12, 1999
INVENTOR(S) : Steven D. Jensen, Dan E. Fischer It is certified that error appears in the above-identified patent and that said Letters Patent is hereby corrected as shown below:

Col 2, ln. 6: after "pre-mixed" change "gells" to --gels--

Col. 3, ln. 37: after "positions" and before "with" delete [a]

Col. 12, ln. 36: after "only as " change "illustrated" to --illustrative--

Signed and Sealed this

Fifth Day of September, 2000

Attest:

Q. TODD DICKINSON

Attesting Officer

*Director of Patents and Trademarks*